United States Patent [19]
Weir et al.

[11] Patent Number: 5,885,844
[45] Date of Patent: Mar. 23, 1999

[54] METHOD OF IDENTIFYING ANALYTES

[75] Inventors: Donald James Weir, Schweiz, Switzerland; Neville John Freeman, Warmingham; Iain Peter May, Harrow, both of United Kingdom

[73] Assignee: EEV Limited, Essex, United Kingdom

[21] Appl. No.: 617,769

[22] PCT Filed: Sep. 21, 1993

[86] PCT No.: PCT/GB93/01985

§ 371 Date: Aug. 5, 1996

§ 102(e) Date: Aug. 5, 1996

[87] PCT Pub. No.: WO95/08765

PCT Pub. Date: Mar. 30, 1995

[51] Int. Cl.⁶ .................................................. G01N 29/20
[52] U.S. Cl. ........................ 436/151; 436/183; 73/24.06
[58] Field of Search .................................... 436/151, 183; 73/24.06

[56] References Cited

U.S. PATENT DOCUMENTS 4,895,017  1/1990  Pyke et al. ................................. 73/23

FOREIGN PATENT DOCUMENTS

| 0 072 744 A3 | 2/1983 | European Pat. Off. . |
| 2 071 323 | 9/1981 | United Kingdom . |
| 2 239 094 | 6/1991 | United Kingdom . |
| WO 83/01511 | 4/1983 | WIPO . |

OTHER PUBLICATIONS

W. Patrick Carey et al. *Anal. Chem. 1987*, 59, 1529–1534.
J.G. Brace et al. *Sens. Actuators 1988*, 14, 47–68.
O.S. Milanko et al. *Anal. Chim. Acta 1992*, 264, 43–52.
M. Ohnishi et al. *Sens. Mater. 1992*, 4, 53–60.
H. Wohltjen et al. *ACS Symp. Ser. 1992*, 508, 86–102.
J.M. Slater et al. *Analyst 1992*, 117, 1265–1270.
L.J. Kepley et al. *Anal. Chem. 1992*, 64, 3191–3193.
M. Nakamura et al. *NTT R&D 1993*, 42, 933–940.

*An automated system for testing surface acoustic wave gas sensors*, A. J. Nederlof, et al., 8127 Review of Scientific Instruments, 64 (1993) Feb., No. 2, New York, US, pp. 501–506.

*An Ultrasonic Flexural Plate–Wave Sensor for Measurement of Diffusion in Gels*, Amy W. Wang, et al., 266b Analytical Chemistry, 65 (1993) Jun. 1, No. 11, Washington, D.C., US, pp. 1639–1642.

*Primary Examiner*—Arlen Soderquist
*Attorney, Agent, or Firm*—Kirschstein et al.

[57] ABSTRACT

A method of identifying an analyte, using a chemical sensor (e.g., a piezoelectric crystal oscillator) which produces an output frequency responsive to different analytes by a characteristic change in the output frequency. The sensor is exposed to a step change (to) in concentration of the analyte and the resulting frequency characteristic measured. An expression for this characteristic is derived consisting of two exponential functions (F, S), one (F) derived from the early part of the frequency characteristic and the other (S) from the latter part. The four parameters ($A_2, A_3, A_4, A_5$) resulting from the functions so obtained are characteristic of the particular analyte.

9 Claims, 1 Drawing Sheet

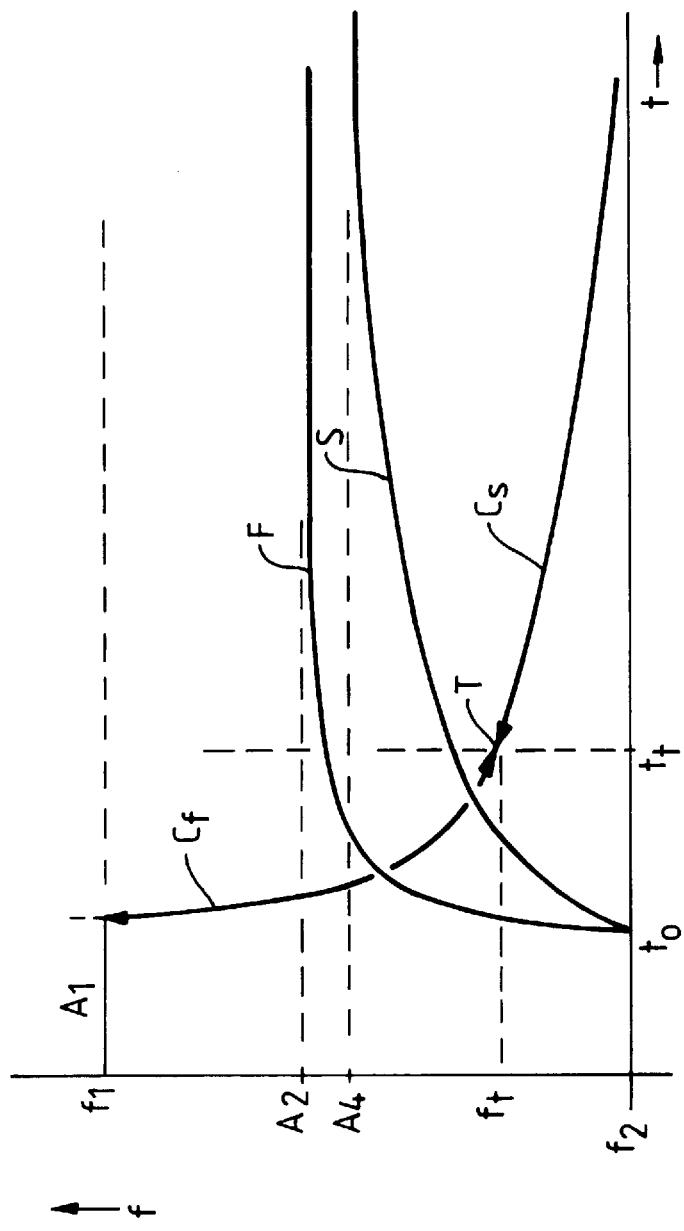

METHOD OF IDENTIFYING ANALYTES

This application is a national stage application based on PCT Application PCT/GB93/01985, filed Sep. 21, 1993.

BACKGROUND OF THE INVENTION

This invention relates to a method of identifying fluid materials, ie analytes, and is particularly but not exclusively concerned with gaseous analytes.

It is known that some materials interact with certain gaseous analytes selectively and that this interaction can be detected from a change in the physical properties of the sensor material, for example, the mass, stiffness or, where the sensor material behaves like a liquid, viscosity. One method of detecting such change is to coat a piezo-electric component with the sensor material, drive the component to oscillate, and measure any change in the oscillation frequency. Devices which exhibit such a response, such as piezo-electric crystal oscillators and surface acoustic wave devices are referred to generically herein as chemical sensors. The change in the properties of the coated device resulting from interaction with the gaseous analyte causes gain and phase changes in the response of the piezo-electric device to applied voltage. This change may be monitored by incorporating the device in an oscillator circuit and monitoring the frequency.

The interaction effect depends upon the nature of the sensor material, ie the coating, and the gaseous analyte. Each sensor material will have a different response to different analytes according to the degree to which the sensor material absorbs, adsorbs, or otherwise interacts with, the analyte.

An important factor in this method of identifying gaseous analytes is the degree to which the interaction effect is reversible. It is important in many applications that when the sensor is withdrawn from a test material which has caused a measurement response the measurement should revert to its original value. Instead of withdrawing the sensor the analyte concentration may be reduced by a purging process, replacing the analyte carrying gas by a carrier gas (eg nitrogen). It is found that, as a general rule, the degree of reversibility varies inversely with the selectivity of the particular sensor material. Thus, if a particular sensor material responds to only a single analyte the interaction is unlikely to be reversible. Such a sensor would have a strong chemical interaction with the analyte.

The weakness and strength of interactions are dependent on thermodynamic and kinetic factors. The thermodynamic factor is to the effect that a low heat of reaction would generally indicate a weak interaction and a high heat of reaction great interaction "strength". However, in certain cases the kinetic factor may be unfavourable to reversibility despite a readily reversible thermodynamic reaction.

A strong interaction resulting from a high heat of reaction cannot of course be made weaker by unfavourable kinetic factors.

With few exceptions then, chemical selectivity for a particular analyte may only be achieved in chemical sensors at the cost of limited reversibility.

This trade-off between chemical selectivity and reversibility may be overcome by the combination of a number of chemical sensors (an array) and pattern recognition. Each sensor in the array may employ a sensor material such as to provide a weak chemical interaction with analytes of interest and therefore a reversible response, and to have a selectivity that is different, if only mildly different, from that of other members of the array. When exposed to a particular analyte the pattern of responses across the array reflects the nature of the analyte in a specific manner. Piezo-electric chemical sensors are particularly appropriate for this approach as they are low cost, easy to fabricate with different chemical selectivities and have the potential for integrating a number of sensors on a single substrate. There is nevertheless the disadvantage of having to employ a relatively complex array rather than a single sensor.

SUMMARY OF THE INVENTION

An object of the present invention is therefore to provide an increased degree of selectivity, without loss of reversibility, for, both, single sensors and arrays.

According to the present invention, in a method of identifying an analyte using a chemical sensor which is arranged to produce an oscillatory output signal and which responds selectively to different analytes by a characteristic change in the frequency of the output signal, the sensor is exposed to step changes (to) in the concentration of the test analyte corresponding to an increase in concentration of the test analyte, and to a decrease in the concentration of the analyte, the sensor output frequency (F) is measured over a period following the respective step changes to provide frequency-time characteristics, and expressions for the characteristics are derived comprising a combination of exponential functions the parameters of the functions being together indicative of the identity of the analyte. It will be appreciated that, in using the term "step change" (in the analyte concentration) it is accepted that there will be a small time delay before the sensor is fully exposed to the new level of concentration owing to the finite dissemination time of the analyte. The step change will not therefore be instantaneous.

The sensor material preferably has a weak interaction with analytes of interest, the interaction being correspondingly reversible. A significant advantage of the reversibility of this method of analyte detection is that the reverse process, ie purging of the analyte gas from its carrier gas, itself produces a different set of parameters providing the basis for analysis.

The parameters may be determined by an iterative method which may employ the Levenburg-Marquadht algorithm.

Initial estimates of the parameters may be obtained by assuming that, for each change in the concentration of the analyte a first exponential function is exclusive to the early part of the characteristic when the response, ie the frequency response, changes rapidly and second exponential function is exclusive to the later part of the characteristic when the response changes more slowly, and determining estimates of the first and second exponential functions from point measurements within the respective parts.

Further selectivity may be obtained by employing a plurality of sensors exhibiting different response characteristics for the same analyte, the parameters derived from the plurality of sensors being together indicative of the identity of the analyte.

The step change in concentration of the test analyte may be an increase or a decrease.

BRIEF DESCRIPTION OF THE DRAWINGS

Reinforcement of the analyte identification may be achieved by using both processes, the increase in concentration being followed, after a period to obtain a stable response, by a decrease in the analyte concentration by purging for example.

DETAILED DESCRIPTION OF THE PREFERRED EMBODIMENTS

A method of identifying gaseous analytes in accordance with the invention will now be described, by way of example, with reference to the accompanying drawing showing a frequency response characteristic for a particular combination of sensor material and analyte.

The accompanying drawing shows the frequency response of a piezo-electric or SAW based chemical sensor, subjected to a "step" change in the ambient concentration of a particular analyte. The characteristic is considered in two parts, the early part $C_f$ and the later part $C_s$ as will be explained. In the absence of analyte the frequency is at a value $f_1$. At a time $t_0$ a step change in the concentration of a test analyte is imposed. The frequency then falls asymptotically towards a lower value $f_2$.

It has been appreciated that the variable component of this frequency-time characteristic can be defined by the sum of two exponential functions. Each of these can be made to yield two parameters, so that four parameters can be obtained from a single sensor even with weak sensor/analyte interaction.

The characteristic is defined as:

$$F(t) = A_1 - A_2(1 - \exp A_3 t) - A_4(1 - \exp A_5 t)$$

F(t) thus being a non-linear function of time, t.

This expression comprises a parameter A associated with the sensor itself and which will be constant for different coating/analyte combinations, and two exponential functions. The first of these, $$A_2(1 - \exp A_3 t)$$

is assumed to have a short time-constant and thus be the "fast" exponential 'F'. The second, $$A_4(1 - \exp A_5 t)$$

is assumed to have a long time-constant ad thus be the slow exponential 'S'. In most cases the time constants of the exponentials are not sufficiently different that these assumptions are true but the process nevertheless leads to reasonable initial values for the subsequent iterative process.

The two exponential components F and S are characteristic of the coating/analyte combination. The parameters $A_2 A_3 A_4$ and $A_5$ are therefore also characteristic of the combination and because of the extra information available from four parameters, the selectivity, ie the ability to identify the test analyte from other, similar analytes, is greatly improved as compared with the basic method of comparing the overall characteristic steady state change $f_1 - f_2$.

The determination of the parameters $A_2 - A_5$ is effected by an iterative approach in which the slope of F( ) as a function of each of the parameters is computed to determine how to alter the parameters to get a better fit on the next iteration. One example of an algorithm which may be employed for this purpose is the Levenburg-Marquadht algorithm.

There is clearly a potential problem since the characteristic function is composed of two parts with the same form and therefore possibly similar slopes. This problem may be overcome by giving the iterative process good initial values for the four parameters. These may be obtained by assuming that the two exponentials have very different time-constants as shown in the drawing, in which $A_2(1 - \exp A_3 t)$ is represented by the fast curve F and $A_4(1 - \exp A_5 t)$ by the slow curve S and fitting one off samples in the first part of the characteristic where frequency changes rapidly and the second off samples in the later part where frequency changes slowly.

It will be noted that, in the early part of the two component characteristics, ie before the (transition) time $t_0$, the slope of the fast exponential (F) is, on average, considerably greater than that of the slow exponential (S). Consequently, if frequency readings are taken in the early part of the frequency transition, ie before $t_1$ the slope, ie the rate of change of frequency, can be attributed largely to the fast exponential. Similarly, in the later part of the characteristic the slope is largely attributable to the slow exponential S, which has not yet "flattened out".

The overall fall in frequency $f_1$ to $f_2$ is known from the frequency-time measurement and the transition frequency $f_1$ can be chosen within this range from trial and error and experience. In the example shown, the transition, from fast exponential dominance to slow exponential dominance, occurs desirably at about nine-tenths of the frequency fall.

A number of frequency readings are then taken prior to the chosen transition (ie at frequencies above f). The frequency may be measured in various ways but it is convenient to count the cycles for fixed periods of, say, 1 second.

The natural logarithm of the frequency values is taken to convert the values to a linear variation. The best fit straight line is derived from the linear values thus giving the slope of the fast exponential in its early portion to a first approximation.

The same process is applied to frequency measurements after the transition time $t_t$ and the slope of the slow exponential in its later portion is derived, again to a first approximation.

The two slopes provide the bases of their respective complete exponentials, and in particular, estimates of the parameters $A_2$ $A_3$ $A_4$ and $A_5$, and on application of the iterative process the refined versions are produced. The parameters $A_2$ and $A_3$ are given by the resulting fast exponential and the parameters $A_4$ and $A_5$ by the slow exponential.

If in fact a greater degree of selectivity were required, because even these four parameters did not define the combination (and therefore the analyte—since the sensor material is known) sufficiently, then an array of sensors, two or preferably more may be employed. These sensors are given different sensor material coatings which all have some affinity for the analyte in question. A set of four parameters is obtained from each sensor in the transition to increased analyte concentration and thus identification can be established with a high degree of confidence.

As mentioned above, a similar analyte identification process can be conducted on the basis of the purging of the analyte from the test gas in cases of weak interaction, the frequency increasing asymptotically from $f_2$ to $f_1$. This further analysis gives a different four parameters $A_6$ to $A_9$ and thus an independent analyte detection. While such analysis on the basis of the purging of the analyte can be used to reinforce the original (increased analyte) analysis, it may also be used alone.

While the greatest advantage from the invention arises from employing weak coating/analyte interactions, it will be appreciated that the same analytical process can be employed with strong interactions, merely increasing the certainty of what will already have been obtained fairly positively.

The example described employed a gaseous analyte in a gaseous test mixture. It will also be possible to employ a liquid analyte in a test liquid when the sensor is responsive, by chemical or physical interaction, to the presence of the analyte.

We claim:

1. A method of identifying an analyte using a chemical sensor which is arranged to produce an oscillatory output signal and which responds selectively to different analytes by a characteristic change in the frequency of the output signal, comprising the steps of: exposing the sensor to step changes in concentration of the analyte corresponding to an increase in the concentration of the analyte, and to a decrease in the concentration of the analyte; measuring the sensor output frequency over a period following the respective step changes to provide frequency-time characteristics; deriving expressions for the characteristics comprising a combination of exponential functions having characteristic parameters which are together indicative of the identity of the analyte; and comparing the characteristic parameters with reference parameters to identify the analyte.

2. The method according to claim 1; and further comprising the step of forming the sensor of a material having a reversible reaction with the analytes.

3. The method according to claim 2; and further comprising the step of employing a plurality of additional chemical sensors exhibiting different frequency-time characteristics for the analyte, and the step of deriving, from the plurality of the additional sensors, additional characteristic parameters which are together indicative of the identity of the analyte.

4. The method according to claim 1; and further comprising the step of determining said characteristic parameters by an iterative method.

5. The method according to claim 4, wherein the determining step is performed by employing the Levenburg-Marquadht algorithm.

6. The method according to claim 4; and further comprising the steps of obtaining initial estimates of said characteristic parameters by assuming that a slope of an early part of each said characteristic is predominantly attributable to a first exponential function and that a slope of a latter part of each said characteristic is predominantly attributable to a second exponential function, and by determining estimates of the first and second exponential functions from point frequency measurements within the respective parts.

7. The method according to claim 1; and further comprising forming said sensor by coating a piezo-electric element with a sensor material which interacts with analytes selectively.

8. The method according to claim 1, wherein the step change corresponding to the decrease in the concentration of the analyte is performed by replacing an analyte-carrying gas by a non-analyte-carrying gas.

9. The method according to claim 1, wherein the deriving step is performed to obtain a first set of the characteristic parameters during said increase in concentration, and a second set of the characteristic parameters during said decrease in concentration, said first set of the characteristic parameters being independent of the second set of the characteristic parameters.

* * * * *